United States Patent [19]

Tanaka et al.

[11] Patent Number: 4,780,277
[45] Date of Patent: Oct. 25, 1988

[54] METHOD AND APPARATUS FOR SUBJECTING GASES TO DISCHARGE TREATMENT

[75] Inventors: Toshio Tanaka, Tokyo; Yasuaki Nagashima, Saitama; Masato Sumiya, Chiba; Shinji Hosono, Tokyo, all of Japan

[73] Assignee: Shinryo Corporation, Tokyo, Japan

[21] Appl. No.: 859,344

[22] Filed: May 5, 1986

[30] Foreign Application Priority Data

| May 10, 1985 | [JP] | Japan | 60-99381 |
| Aug. 5, 1985 | [JP] | Japan | 60-172072 |
| Sep. 6, 1985 | [JP] | Japan | 60-197229 |
| Oct. 24, 1985 | [JP] | Japan | 60-238375 |
| Oct. 31, 1985 | [JP] | Japan | 60-245147 |

[51] Int. Cl.$^4$ .................. A61L 9/015; A61L 9/20
[52] U.S. Cl. .................. 422/4; 422/22; 422/24; 422/30; 422/172; 204/176; 423/212; 423/219
[58] Field of Search .................. 422/121–123, 422/4, 22, 30, 169, 172, 177, 24; 423/212, 219; 204/176

[56] References Cited

U.S. PATENT DOCUMENTS

| 4,315,837 | 2/1982 | Rorrke et al. | 422/122 |
| 4,348,357 | 9/1982 | Bithell | 422/22 |
| 4,551,304 | 11/1985 | Holten et al. | 422/122 |

FOREIGN PATENT DOCUMENTS

| 23147 | 8/1979 | Japan . |
| 108511 | 8/1981 | Japan . |
| 1573802 | 8/1980 | United Kingdom . |

OTHER PUBLICATIONS

CA. 81(2), 5953v, Chemical Abstracts, 1974.
CA. 104(23), 205572a, Chemical Abstracts, 1986.

*Primary Examiner*—Barry S. Richman
*Assistant Examiner*—Jill Johnston
*Attorney, Agent, or Firm*—Browdy and Neimark

[57] ABSTRACT

A waste gas in treated by the sequence of discharge treatment and catalytic oxidation. A microbe-containing gas is disinfected by first mixing it with ozone, then subjecting the gas to discharge treatment and catalytic reaction successively.

18 Claims, 8 Drawing Sheets

METHOD AND APPARATUS FOR SUBJECTING GASES TO DISCHARGE TREATMENT

BACKGROUND OF THE INVENTION

1. Field of the Invention

The present invention relates to a method and apparatus for the discharge treatment of gases. More particularly, the present invention relates to a method of treating noxious components in off-gases from factories or the like by catalytic oxidation. The present invention also relates to a method of disinfecting the air or the surfaces of various objects with the aid of ozone. The present invention additionally relates to a discharge method and apparatus which may be employed in these methods.

2. Prior Art

A variety of methods have heretofore been proposed and practiced in order to treat waste gases in manners that best suit the properties of the target components in the gases. For example, the air that is evolved in wastewater treatment plants and which contains such noxious components as hydrogen sulfide and mercaptan is usually treated by absorption, adsorption, oxidation or masking techniques. Of these methods, the catalytic oxidation process which employs platinum-alumina catalysts is considered to be most advantageous because of its high elimination efficiency.

Gases containing organic solvents are discharged from petrochemical plants and printshops or printworks. The organic solvents are recovered by the combination of adsorption on activated carbon and regeneration of steam if the concentrations of the organic solvents are as high as a few percent. Treatment by catalytic oxidation is performed if the concentrations of the organic solvents are on the order of $10^2$ ppm.

It has been proposed that boiler off-gases containing sulfurous acid should be treated by catalytic oxidation with vanadium catalysts, rather than by wet adsorption with calcium carbonate, in order to recover sulfuric acid.

As illustrated above, catalytic oxidation is being used increasingly as a method for treating waste gases. The catalytic oxidation process has the advantage of permitting lower reaction temperatures to be employed than the direct oxidation method but it still needs temperatures in the range of from about 200° to 400° C. in order to attain satisfactory results. Not only does this require increased energy costs in heating the gas to be treated but it also cases adverse effects on the lifetime of the catalyst employed. The catalysts employed in the conventional catalytic oxidation methods generally have lifetimes ranging from 1 to 2 years.

With the recent advances of medical technology, the interflow of personnel and equipment has increased in medical facilities and this is causing an increase in the chance of cross infection in patients. Waiting rooms in hospitals are particularly vulnerable to cross infection originating from outpatients. Therefore, an increasing number of medical facilities today have introduced sanitizing air conditioners as infection preventing means. The need for a sanitary environment has also been recognized in the food industry and bioclean rooms are being increasingly adopted by manufacturers of aseptically packed longlife foods.

Practically all of the methods practiced today for disinfecting air have relied upon the use of air filters. In this system, the air to be treated is passed through filters such as to trap both dirt and microorganisms with the resulting clean germ-free air being supplied into the clean room. The disadvantages of this system are as follows: increased electric energy costs for blowers will result from the pressure drop across the filters; a need exists for the maintenance of the filters; and insufficient maintenance of the filters may lead to contaminated air ducts and allow germ-containing air to be supplied into a clean room.

Sterilization of air by ozone has been proposed as an alternative to the use of air filters (see, for example, Unexamined Published Japanese Patent Application No. 115593/77). Ozone has been known to have a sterilizing action. Ozone itself is decomposed to harmless oxygen and hence is considered to be an advantageous air sterilizer. However, the clean air obtained by sterilization with ozone has residual ozone present. Ozone is harmful to humans even if it is present in low concentrations and generally its content in working areas must not exceed 0.1 ppm. In order to meet this requirement, the residual ozone in the clean air must be degraded by some means such as the spontaneous decomposition method or the thermal decomposition method. Ozone is a chemically highly labile substance and decomposes to oxygen upon standing. However, the half life of ozone at ordinary ambient temperatures is comparatively long (ca. 16 hours) and this makes the spontaneous decomposition method unsuitable for commercial use. The thermal decomposition method requires high operating costs for heating purposes and the air must be cooled to ambient temperature after heat decomposition. It is therefore difficult to integrate the thermal decomposition method into air conditioning systems. The applicant of the present invention previously proposed a method of degrading ozone by microwave energy (see Japanese Patent Application No. 8275/1984). Although this method has eliminated the defects of the conventional techniques of ozone decomposition, it still has the disadvantages of low energy efficiency and the need for using an expensive apparatus.

The second problem encountered in applying ozone sterilization to air conditioning systems is its slow effect. The rate of sterilization by ozone depends on its concentration but usually ozone must be held in contact with air for a period no shorter than several hours. Therefore, considerable difficulty exists in applying the conventional techniques of ozone sterilization to air conditioning systems which are required to disinfect a large volume of air.

The applicant of the present invention previously developed an improved method of ozone sterilization in Japanese Patent Application No. 98432/1984 (laid open for public disclosure Nov. 30, 1985). This method is characterized by performing discharge treatment on air containing both ozone and unwanted microorganisms such that ozone decomposition is carried out simultaneously with the killing of the microorganisms.

Discharge apparatus are currently used in a variety of fields. For example, they are incorporated in ozone generators or precipitators which remove dust particles from waste gases by electrostatic precipitation. Discharge apparatus are also being used for sterilization and deodorization purposes by making use of the characteristic features of the discharge phenomenon.

The conventional discharge apparatus forms a nonuniform electric field between electrodes (which may either be two needles or one may be a needle and the other a plate) and generates a corona discharge, glow discharge, arc discharge or spark discharge by establishing appropriate discharge conditions. Whichever type of discharge is selected, the phenomenon of discharge itself is unstable and a plurality of electrode pairs must be provided in order to produce the desired electric field in an industrial-scale apparatus. If the electrodes are directly connected to the power source, it is difficult to obtain a uniform and stable discharge at all discharge gaps because the state of the fluid to be treated is not necessarily uniform at each of the discharge gaps; and the discharge gap length may differ slightly from one gap to another. In addition, the abrupt increase in current upon discharging may break some or all of the electrodes. In order to avoid these problems, the conventional discharge apparatus has a resistor incorporated in the circuit connecting an electrode to the power source (see, for example, Japanese Patent Publication No. 23147/1979). Since the resistor is provided for each electrode, an increase in the number of electrodes incorporated in the apparatus must be accompanied by a corresponding increase in the number of resistors. A further problem arises from the fact that all the power consumed by the resistors is dissipated as heat and will not contribute at all to the efficiency of discharge.

SUMMARY OF THE INVENTION

One object, therefore, of the present invention is to propvide a method which is capable of catalytic oxidation of waste gases at temperatures lower than those necessary in the prior art methods.

Another object of the present invention is to provide a method for sterilizing a gas with ozone which is capable of performing the decomposition of ozone and the sterilization of the gas simultaneously in an energy-conserving manner.

Still another object of the present invention is to provide a discharge apparatus that is capable of producing a stable discharge and which is suitable for the purposes of treating a waste gas by catalytic oxidation and of sterilizing the gas with ozone.

The present invention provides a method of treating noxious components in a waste gas by oxidation which comprises first introducing the waste gas into a discharge zone to form a plasma-containing gas and, then, introduing said plasma-containing gas into a catalytic reaction zone so as to allow said noxious components to enter into a catalytic oxidation reaction.

The present invention provides a sterilization method which comprises: adding ozone to a gas containing microorganisms; introducing the resulting ozone-containing gas into a discharge zone so as to produce plasma in the gas; and supplying the resulting treated gas into a catalytic reaction zone at ordinary ambient temperature such that a gas which is substantially free from ozone and microorganisms is obtained.

The present invention provides a discharging method wherein a discharge is produced while the stream of a fluid to be treated is allowed to flow at a rate of at least 5 m/sec through a discharge gap formed between electrodes which are arranged in a face-to-face relationship for voltage application.

The present invention provides a discharge apparatus comprising electrodes which are arranged in a face-to-face relationship for voltage application and at least one intermediate electrode which is positioned on the line connecting the discharge areas of said two voltage impressing electrodes, said intermediate electrode being disposed between said voltage impressing electrodes and spaced from the latter.

The present invention also provides a waste gas treating apparatus or a gas disinfecting apparatus which incorporates the above-described discharge apparatus.

PREFERRED EMBODIMENTS OF THE INVENTION

Figure 1:
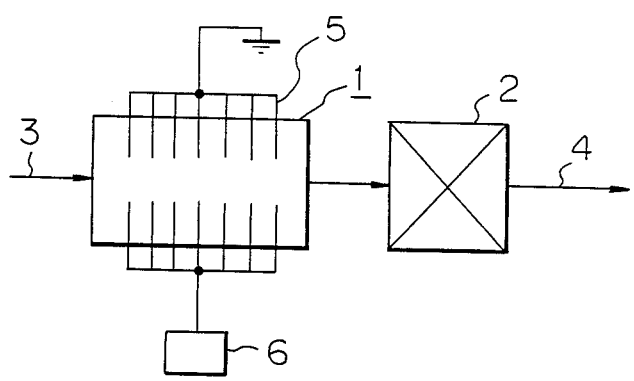
FIGS. 1 and 2 are schematic diagrams showing two different methods of treating waste gases in accordance with the present invention.

The present invention is hereunder described in detail with reference to the accompanying drawings. FIG. 1 is a schematic diagram showing one embodiment of the method of treating a waste gas in accordance with the present invention. As shown, the system employed in this method comprises two main sections, a discharge zone 1 and a catalytic reaction zone 2. The waste gas to be treated flows into the discharge zone 1 through a line 3 and plasma is formed in the waste gas in zone 1 as a result of the discharge which may take place in the manner to be described below. The plasma-containing gas then enters the catalytic reaction zone 2 where the noxious components in the waste gas are catalytically oxidized and the resulting oxidation products in a gaseous form are rejected from the system through a line 4.

The method of the present invention enables treatment of every type of the waste gases that are conventionally treated by catalytic oxidation. The waste gases that can be treated by the method of the present invention are those which contain: malodorous components such as hydrogen sulfide, mercaptans (e.g. methyl mercaptan), ammonia, and amines (e.g. trimethylamine); organic solvents such as benzene, xylene, toluene, butyl CELLOSOLVE ™ (ethylene glycol monobutyl ether), methyl ethyl ketone, methyl isobutyl ketone, methanol, isoamyl alcohol, phenol, isopropyl alcohol, trichloroethylene, acetone, tetrachloroethylene, methyl acetate, ethyl acetate, butyl acetate, and normal hexane; and gaseous inorganic oxides such as nitrogen oxides ($NO_x$), sulfur oxides ($SO_x$) and carbon monoxide (CO).

In accordance with the present invention, a waste gas containing one or more of the components listed above (hereinafter referred to as "noxious components") is introduced into the discharge zone 1, where electrode pairs 5 each consisting of two members facing each other are arranged at predetermined intervals. A power supply 6 provides a specified a.c. or d.c. voltage to the individual electrodes.

The discharge which occurs within zone 1 is either a corona or glow discharge, with the latter being preferable. Glow discharge is a self-sustaining phenomenon which occurs in the period of transition from a spark discharge to an arc discharge. The discharging conditions which may be employed in zone 1 are: a field strength on the order of from $10^3$ to $10^4$ volts/cm, and a discharge current ranging from a few milliamperes to several tens of milliamperes. The input power will vary with the degree of contamination of the waste gas to be treated and ranges from a few watts to several tens of watts per $m^3$/hr of the gas. Preferably, a d.c. negative voltage is applied to the electrodes. The waste gas is permitted to stay within the discharge zone 1 for a sufficient period of time of form a plasma of the noxious components. The discharge zone needs a space velocity (SV) ranging from approxiamately $10^3$ to $6 \times 10^4$ $hr^{-1}$.

The waste gas containing the plasma formed in the discharge zone 1 is introduced into the catalytic reaction zone 2 where the noxious components are catalytically oxidized at ordinary ambient temperature. Various catalysts may be used in the present invention and they include solid acid catalysts such as synthetic zeolite and a silica-alumina catalyst; activated carbon; and lead-, copper-, zinc- and nickel-supporting catalysts. Activated carbon is particularly advantageous for use in the treatment of $SO_x$ and may also serve to adsorb the sulfuric acid which is one of the reaction products of oxidation of $SO_x$. The ionized noxious components will react with the oxygen (presumably ionized) in the waste gas on the surface of the catalyst, thereby forming corresponding oxides.

The foregoing description assumes that the waste gas to be treated is an oxygen-containing gas such as one containing air as its principal component. If the waste gas contains no oxygen, it may be mixed with oxygen or ozone before it is supplied into the discharge zone. The use of ozone is particularly advantageous if the noxious components are present in high concentrations or if their rate of catalytic oxidation is slow.

One advantage of the present invention is that it allows the catalytic reaction to take place at ordinary ambient temperature, thereby eliminating the energy cost conventionally required for heating the gas to be treated. A further advantage results from the fact that ordinary ambient tempreature prevails in the catalytic reaction zone: the catalyst will be deteriorated very slowly and, hence, its lifetime is significantly prolonged. One reason for the economic disadvantage of the prior art process is its use of a platinum catalyst but the present invention which permits the use of a non-previous metal catalyst such as zeolite or silica-alumina catalyst realizes an appreciable reduction in the initial cost.

Furthermore, the process of the present invention accommodates a wide range of variations in the concentrations of noxious components in the waste gas by means of simply controlling the power input to the discharge zone.

Figure 2:
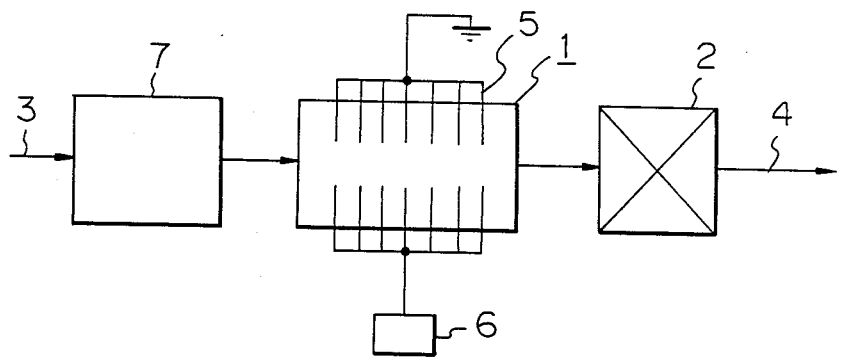

Another embodiment of the method of the present invention for treating waste gases is hereunder described with reference to the diagrammatic view shown in FIG. 2, wherein the system consists basically of a discharge zone 1, a catalytic reaction zone 2 and a heating zone 7. The waste gas to be treated is fed through a line 3 and enters the heating zone 7 where it is heated up to a predetermined temperature. The heated gas then flows into the discharge zone 1 where plasma is formed in the waste gas as a result of the discharge which may take place in the manner to be described below. The plasma-containing gas then enters the catalytic reaction zone 2 where the noxious components in the waste gas are catalytically oxidized and the resulting oxidation products in a gaseous form are rejected from the system through a line 4.

The waste gas to be heated in the heating zone 7 contains one or more of the noxious components listed above. This waste gas is usually at ordinary ambient temperature and, according to the second embodiment of the present invention, is heated to at least 40° C. As will be demonstrated in Example 5 to be given later in this specification, the efficiency of the process of the present invention increases with the increase in the temperature of the waste gas. However, if the waste gas is heated excessively to temperatures in the range, for example, of 200°–400° C., the increased throughput is cancelled by the following deleterious effects: the temperature level is no lower than what is employed in the conventional methods of catalytic oxidation and the advantage of using the discharge zone is not attained; the high temperature of the waste gas also causes adverse effects on the lifetime of the catalyst; and, needless to say, the energy cost of heating the waste gas is increased. In consideration of these factors, the waste gas to be treated by the method of the present invention is preferably heated to temperatures between 40° C. and 100° C., more preferably between 40° C. and 60° C.

The waste gas may be heated by conventional means and the direct combustion method using a heavy oil or otherwise fueled burner placed within the waste gas may be used with advantage. If the noxious components are inflammable and their concentrations in the waste gas are close to the explosion limit, indirect heating employing a heat exchanger may be used. Since the waste gas needs to be heated by only several tens of degrees in Celsius, heating by dilution with a hot gas may also be employed.

In accordance with the second embodiment of the method of the present invention, catalytic reaction can be carried out at temperatures significantly lower than what are employed in the conventional catalytic oxidation processes, and this enables a reduction in the energy cost required for heating the waste gas to be treated by the prior art methods. The throughput of this embodiment is three to four times as great as that of the first embodiment which performs catalytic oxidation of noxious components at ordinary ambient temperatures, and this allows a smaller apparatus to be used in the treatment of the waste gas.

The mechanism or operating theory of the treatment of waste gases by the process of the present invention has not been fully unravelled, but taking $SO_2$ as an example of the noxious component to be removed, the following reactions would proceed in the treatment by the present invention:

(1) SO$_2$-containing air supplied to the discharge zone is energized by a glow or corona discharge-producing field and the individual components of the gas are ionized to form two types of plasma:

$$SO_2 \xrightarrow{e^-} SO_2^*(g) \longrightarrow SO_2^*(a)$$

$$O_2 \xrightarrow{e^-} O_2^*(g) \longrightarrow O_2^*(a)$$

where (g) denotes that the substance with that suffix is in the gaseous form and (a) signifies that the substance with that suffix is adsorbed;

(2) When the air containing the two types of plasma is introduced into the catalytic reaction zone, the ionized molecules, SO$_2^*$(g) and O$_2^*$(g), react with each other, permitting the following reaction to proceed on the surface of the catalyst at ordinary ambient temperature:

$$SO_2^*(a) + \tfrac{1}{2}O_2^*(a) \rightarrow SO_3$$

The resulting SO$_3$ reacts with the moisture in the air to form sulfuric acid which then is adsorbed on the surface of the catalyst.

The advanages resulting from the increase in the temperature of the waste gas are apparent in both the discharge zone and the catalytic reaction zone. In the discharge zone, the increased temperature of the waste gas would increase the rate at which the active molecules are evolved and, in the catalytic reaction zone, it would increase the frequency of contact between the so formed active molecules.

One preferred embodiment of the disinfection method of the present invention is hereunder described with reference to the schematic diagram in FIG. 3. The system shown in FIG. 3 consists essentially of an ozone generating zone 31, a mixing zone 32, a discharge zone 33, a catalytic reaction zone 34, and a working space 35. Air drawn from the working space 35 with a blower B is supplied into the mixing zone 32 where the air is mixed with the ozone generated in zone 31. The resulting mixture of ozone and air is sent to the discharge zone 33 where ozone is decomposed into the atomic oxygen. The resulting air is fed into the catalytic reaction zone 34 where the residual ozone in the air is decomposed and the residual microorganisms destroyed. The resulting clean air is circulated through the working space 35 to produce a germ-free atmosphere.

The working space 35 may be any of the spaces that require a germ-free atompshere, such as bioclean rooms (e.g. surgical operating rooms), waiting rooms in hospitals, and buildings at food producing plants and pharmaceutical factories. The method illustrated in FIG. 3 enables a germ-free atmosphere to be supplied into the working space 35 without introducing any ozone into that space and this offers a safe technique for supplying a germ-free atmosphere into operating rooms, waiting rooms in hospitals and other spaces to be occupied by humans.

The air drawn from the working space 35 is sent to the mixing zone 32 where it is mixed with ozone. The ozone generating zone 31 may employ any conventional ozone generator such as a silent corona-discharge ozone generator or an ozone bomb. The ozone concentration in the mixing zone 32 may range widely from a few ppm to the order of 10$^3$ ppm. The ozone-air mixture may be allowed to stay within the mixing zone 32 for a sufficient period of time to disinfect the air to some extent. However, as will be described later in this specification, the synergism of ozone and the atomic oxygen evolved in the discharge zone 33 produces a satisfactory sterilizing effect, so the residence time of the ozone air in the mixing zone 32 may be reduced to such a level that the zone 32 is replaced by a duct through which ozone is injected into the air stream.

The ozone-air mixture issuing from the mixing zone 32 is introduced into the discharge zone 33 where a discharge is permitted to take place. The discharge which occurs in the zone 33 is either a corona, arc or glow discharge, with glow discharge being preferable. Glow discharge is a self-sustaining phenomenon which occurs in the period of transition from a spark discharge to an arc discharge. The discharging conditions which may be employed in zone 31 are: a field strength on the order of from 10$^3$ to 10$^4$ volts/cm, and a discharge current ranging from a few milliamperes to several tens of milliamperes. The input power will vary with the degree of contamination of the air to be treated and ranges from a few watts to several tens of watts per m$^3$/hr of the air. A d.c. negative voltage is preferably applied to the electrodes. The gas is allowed to stay within the discharge zone 33 for a sufficient period of time to produce plasma. The space velocity (SV) necessary in the discharge zone generally ranges from about 10$^3$ to about $6 \times 10^4$ hr$^{-1}$.

Figure 4:
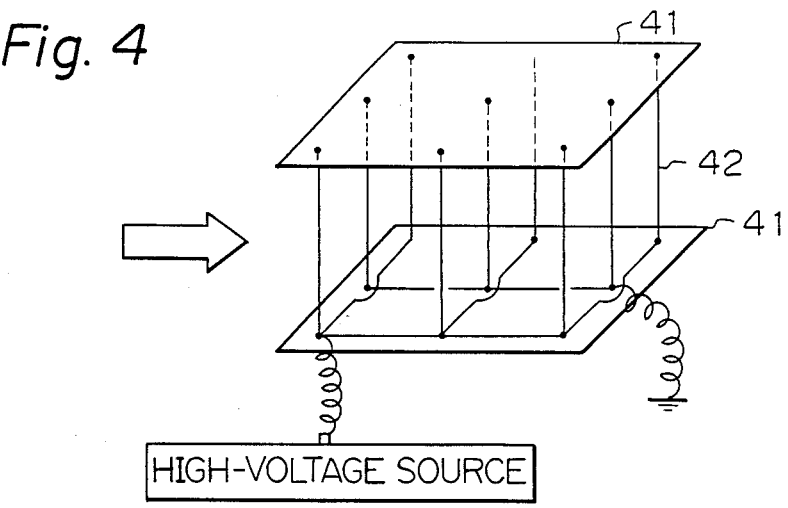
FIGS. 4 and 5 are schematic diagrams showing preferred embodiments of the discharge apparatus employed in the sterilization method of the present invention.

FIG. 4 is a diagrammatic perspective view of the discharge apparatus which is suitable for use in the discharge zone incorporated into the system of the present invention. As shown, the discharge apparatus consists of a pair of insulating frames 41 and a plurality of parallel wire electrodes 42 which are fixed thereto in such a manner that a high d.c. voltage can be applied between electrodes. When an ozone-containing fluid is passed between electrodes, the ozone is decomposed by corona discharge and a stream of fluid having a lowered ozone concentration results. The material of the wire electrodes 42 is not critical but tungsten is used with advantage. The inter-electrode distance is determined by such factors as the flow rate of the fluid to be treated and the discharge voltage. A typical electrode-to-electrode distance ranges from a few centimeters to several tens of centimeters.

Figure 5:
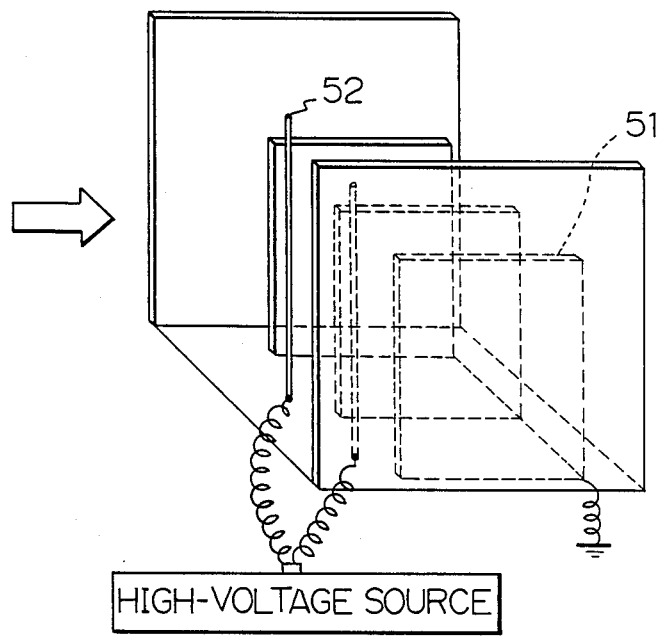

FIG. 5 is a schematic perspective view showing another embodiment of the discharge apparatus. As shown, the apparatus according to this embodiment consists of an array of parallel plate electrodes 51 and wire electrodes 52, wherein the wire electrodes placed in front of or at the back of the plate electrodes are spaced apart at equal distances. Preferably, the wire electrodes 52 are used as cathodes. The electrons produced as a result of discharge serve to degrade or ionize ozone, thereby realizing effective ozone decomposition.

The plasma-containing gas obtained in the discharge zone 33 (see FIG. 3) is then introduced into the catalytic reaction zone 34 where both decomposition of the residual ozone in the gas and killing of the microorganisms in the same gas are accomplished. Various catalysts may be used in the present invention and they include solid acid catalysts such as synthetic zeolite and a silica-alumina catalyst; activated carbon; and lead-, copper-, zinc- and nickel-supporting catalyst. Solid acid catalysts, particularly synthetic zeolite catalysts, are preaferable. The catalyst may assume any form such as a sphere or pellet. The space velocity in the catalyst bed will not be limited to any particular value but it generally ranges from $10^3$ to $10^5$ hr$^{-1}$, preferably $10^4$ to $10^5$ hr$^{-1}$. Catalytic reaction may be carried out at ambient temperature and at atmospheric pressure.

Figure 3:
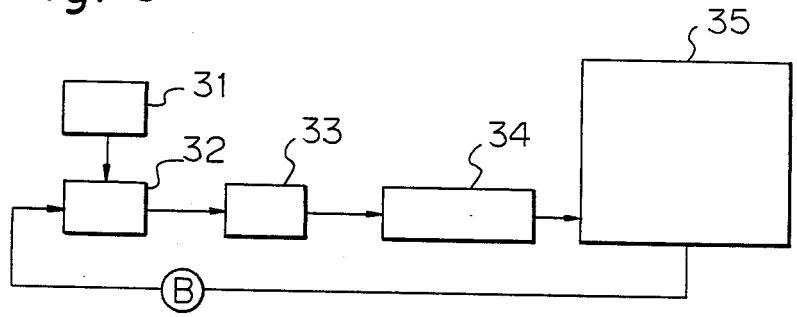
FIGS. 3, 6 and 7 are schematic diagrams showing preferred embodiments of the sterilizing method of the present invention.

In the embodiment shown in FIG. 3, the fluid to be disinfected is drawn from the working space 35 but it should be understood that the present invention may adopt the "noncirculating" system wherein the outdoor air is introduced into the mixing zone 32 and supplied into the working space 35 after being disinfected. In addition to air, inert gases such as nitrogen gas may also be treated by the present invention.

Figure 6:
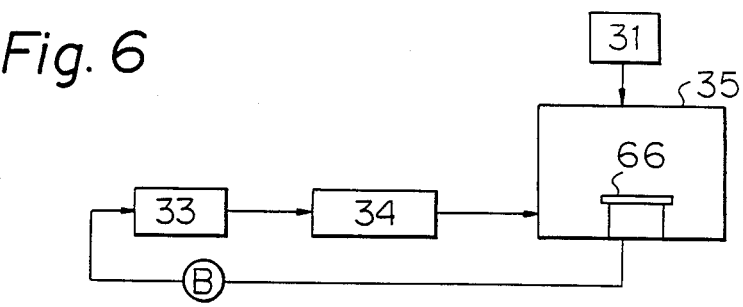

FIG. 6 is a schematic diagram showing still another embodiment of the disinfecting method of the present invention. This embodiment is effective for the purpose of sterilizing miscellaneous germs on the wall surfaces of the working space 35 or on the operating table 66 or other objects in the working space 35. After the ozone generated in the zone 31 is introduced into the working space 35, it is left there for a few hours until surface disinfection is complete. Subsequently, the ozone-containing air is drawn from the working space by a blower B and sent to the discharge zone 33 where the residual ozone is decomposed into oxygen. The ozone-free air is then returned to the working space 35.

Figure 7:
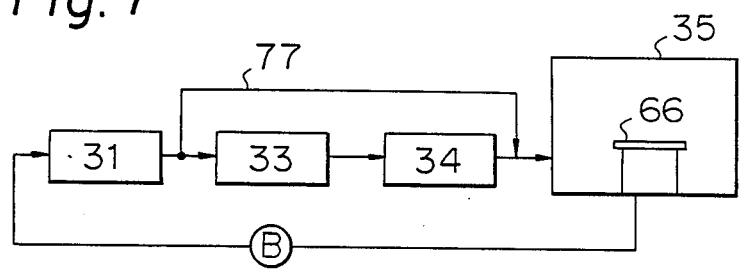

FIG. 7 is a schematic diagram showing a further embodiment of the disinfecting method of the present invention. In this embodiment, air is drawn from the working space 35 with a blower B and fed into the ozone generating zone 31 where it is mixed with the generated ozone. The resulting ozone-containing air is sent to the working space 35 through a bypass 77. After sterilization of the surface of the wall, ceiling or objects in the working space 35 is completed, the bypass 77 is closed and the ozone generator is turned off and the air in the working space 35 is fed successively into a discharge zone 33 and a catalytic reaction zone 34, and the resulting ozone-free clean air is returned to the working space 35.

Formalin is chiefly used in the conventional practice of surface disinfection of the type contemplated in the embodiments shown in FIGS. 6 and 7. However, formalin disinfection has the disadvantages of residual formalin being left on the surface of the treated object and of the need for its removal. These problems are entirely absent from the process of the present invention since the ozone in the air is completely decomposed into oxygen.

To their great surprise, the present inventors have found that when ozone-containing air is brought into contact with a catalyst after passage through the discharge zone, the ozone is decomposed into oxygen while almost all of the miscellaneous germs in the air are killed. In order to perform thorough disinfection of air with ozone alone, the air must be held in contact with ozone for at least a few hours. In addition, the residual ozone must be removed from the resulting "clean" air after it is decomposed into oxygen. It has been found that in accordance with the method of the present invention, ozone decomposition and killing of unwanted microorganisms which are two seemingly incompatible requirements can be satisfied simultaneously and within a very short period. Stated more specifically, in accordance with the present invention, the ozone-containing air is introduced into the discharge zone where a discharge is produced with a low level of electric power to thereby accomplish both partial decomposition of ozone (e.g. 80% ozone decomposition) and killing of unwanted microorganisms. Subsequently, the air containing the residual ozone and living microorganisms is fed into the catalytic reaction zone where complete ozone decomposition and microbial sterilization are effected.

The power employed in the discharge zone according to the present invention is preferably not higher than about 60% of the power required for accomplishing complete decomposition of ozone by an electrical discharge.

The mechanism by which ozone decomposition and microbial sterilization take place in the present invention would be as follows. When ozone-containing air is discharged, electrons are emitted and will react with the highly reactive ozone molecule:

$$O_3 + e \rightarrow O_2 + (O) \qquad (1)$$

The atomic oxygen (O) is extremely short-lived but is so reactive that it will almost immediately react with another ozone molecule to form two oxygen molecules:

$$O_3 + (O) \rightarrow 2O_2 \qquad (2)$$

The reaction denoted by Equation (1) is believed to be the rate-limiting step in the reaction of ozone decomposition and, by performing a discharge treatment in the present invention, the reaction expressed by Equation (1) would proceed at a rapid rate.

The atomic oxygen (O) displays a strong oxidizing action and will readily bind to carbon or hydrogen atoms in organic matter and oxidatively decompose the latter into carbon monoxide, carbon dioxide or water vapor. If the organic matter was unwanted microorganisms in air, they would become extinct by being oxidatively decomposed with path of the reactive oxygen atoms that have evolved as a result of ozone decomposition.

As mentioned earlier in this specification, the air issuing from the discharge zone used in the method of the present invention contains both undecomposed ozone and living microorganisms. When this air is passed into the catalytic reaction zone, the reaction expressed by Equation (2) would take place on the surface of the catalyst with ozone being decomposed into molecular oxygen ($O_2$). On the other hand, the residual living microorganisms would be trapped on the surface of the catalyst where they are decomposed oxidatively by ozone or reactive atomic oxygen.

In accordance with the disinfection method of the present invention, the power requirement for producing a discharge is reduced by at least 40% of the value required in the prior art techniques. Since the necessary catalytic reaction can be carried out at ordinary ambient temperatures, the catalyst employed will not be deteriorated rapidly and hence exhibit a prolonged service life. In addition, the method of the present invention permits the use of a non-precious metal catalyst such as zeolite which involves only a low maintenance cost. Another advantage of the catalytic reaction zone is that variations in the ozone addition will exert no adverse effects on the quality of the outgoing air stream.

In the forgoing pages, the methods of waste gas treatment and microbial sterilization in accordance with the present invention have been described. We now describe the discharge method and apparatus which are suitable for use in these methods.

In the discharge method, a high-speed gas stream is caused to flow through discharge gaps. The gas stream must flow at a rate of at least 5 m/sec. At lower flow rates, the desired discharge stability cannot be attained. Above 5 m/sec, the discharge stability is increased with increasing flow rate. However, the flow rate is preferably not higher than 30 m/sec since above that value, the static pressure loss increases with an attendant increase in the energy cost of operating the blower. The flow rate at a discharge gap is that of the gas flowing in a direction perpendicular to the line connecting the discharge area of each electrode. For the purposes of the present invention, it is preferable that the flow rate requirement specified above is satisfied at all of the discharge gaps employed. It should however be noted that the desired discharge stability can be attained if said flow rate requirement is met at only some of the discharge gaps.

In addition to air, other gases such as oxygen and nitrogen can be treated by an electrical discharge in accordance with the method of the present invention. These gases may contain ozone and other components if the specific object of the method permits. If the residence time of the gas in the discharge apparatus is long, the outgoing gas may be recycled to the inlet of the same apparatus such as to maintain the necessary flow rate of the gas. This is effective in reducing the overall size of the apparatus.

The discharge which takes place in the method of the present invention may be a glow, arc or spark discharge, with the glow discharge being preferable.

Figure 8:
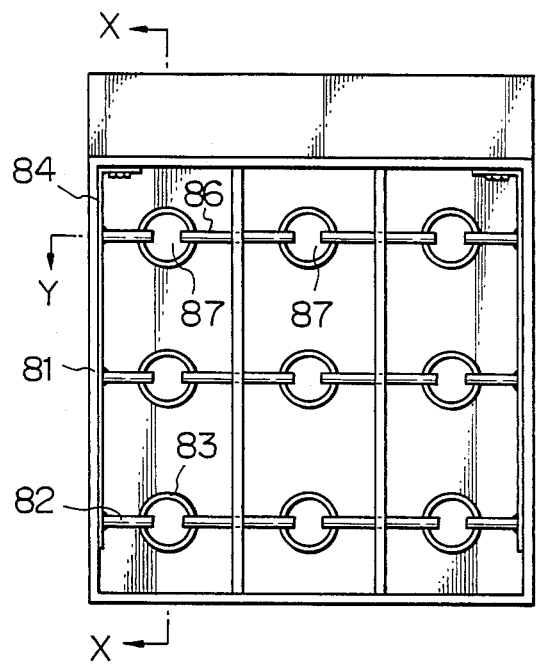
FIG. 8 is a front view showing one embodiment of the discharge apparatus of the present invention.
Figure 9:
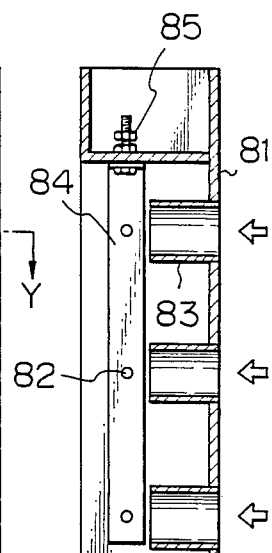
FIG. 9 is a cross section taken on line X—X of FIG. 8.
Figure 10:
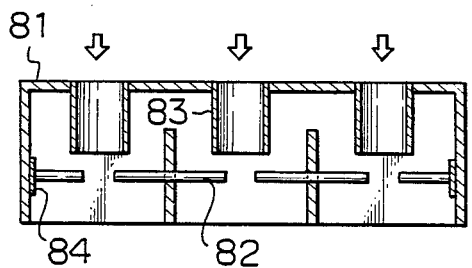
FIG. 10 is a cross section taken on line Y—Y of FIG. 8.

FIG. 8 is a front view of the discharge apparatus which may be employed in practicing the method of the present invention. FIG. 9 is a cross section taken on line X—X of FIG. 8, and FIG. 10 is a cross section taken on line Y—Y of FIG. 8. A rectangular electrode supporting frame 81 is provided with two strips of current supplying conductor 84 which run on the inner surfaces of two opposite sides of the frame. The conductor strips 84 are joined to the frame 81 by terminals 85. The conductor strips 84 are provided with rod-shaped voltage impressing electrodes 82 which are spaced at substantially equal distances and are disposed such that the electrodes on one side of the frame 81 will respectively face those on the opposite side of the frame. A plurality of intermediate electrodes 86 are provided at predetermined intervals on the line connecting the tips of two opposed voltage impressing electrodes 82. No voltage will be impressed on the intermediate electrodes. The use of the intermediate electrodes is optional in the present invention, and if they are not used, a discharge gap may be formed by bringing the two opposed voltage impressing electrodes 82 closer such that the tip of one electrode will face that of the other.

In the embodiment shown in FIG. 8, a discharge gap 87 is formed between the tip of one voltage impressing electrode 82 and the tip of an adjacent intermediate electrode 86 and between two adjacent intermediate electrodes which face each other at the tip. A tubular nozzle 83 is provided for each discharge gap 87 in such a manner that one open end thereof faces said gap. The gas is fed through the tubular nozzles 83 such that the desired flow rate within the range specified above will be attained at each of the discharge gaps 87.

Figure 11:
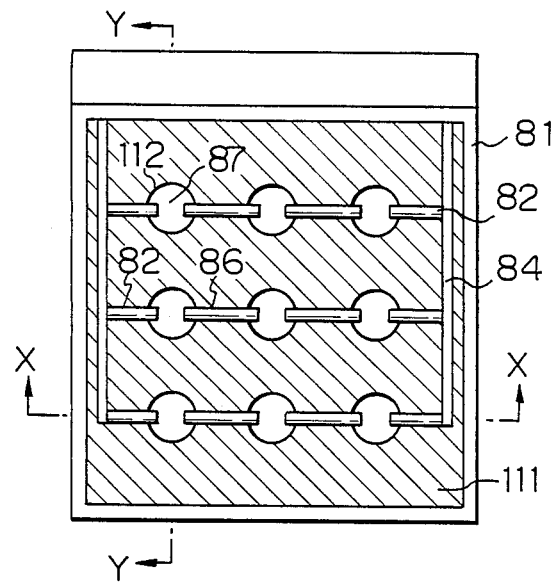
FIG. 11 is a front view showing another embodiment of the discharge apparatus of the present invention.
Figure 13:
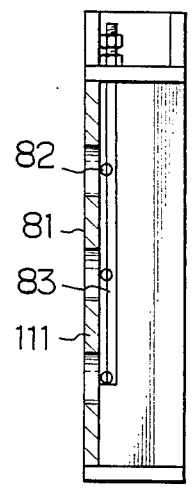
FIG. 13 is a cross section taken on line Y—Y of FIG. 11.
Figure 12:
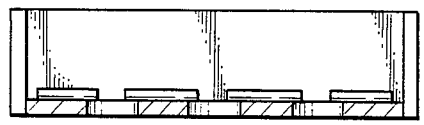
FIG. 12 is a cross section taken on line X—X of FIG. 11.

FIG. 11 is a front view showing another embodiment of the discharge apparatus which may be used with advantage in practicing the method of the present invention. FIG. 12 is a cross section taken on line X—X of FIG. 11 and FIG. 13 is a cross section taken on line Y—Y of FIG. 11. The electrode array employed in this embodiment is the same as what is shown in FIG. 8 and the only difference is that the tubular nozzles are replaced by a perforated plate 111, which is placed in close proximity to the electrodes such that the holes 112 in the plate 111 will align with respective discharge gaps 87. The channell for the passage of the gas to be treated, say, air, is restricted by the perforated plate 111 but it will flow through the holes 112 providing the desired flow rate at the individual discharge gaps.

In accordance with the present invention, a gas stream having the desired speed is caused to flow through the discharge gaps and this enables an electrical discharge to take place more consistently than is possible with the prior art techniques. As will be shown later in Example 8, the variation in the discharge current applied in the method of the present invention can be reduced to less than half of the value experienced in the prior art methods. The present invention has the additional advantage of uniformity in the discharge taking place at individual discharge gaps.

Figure 14:
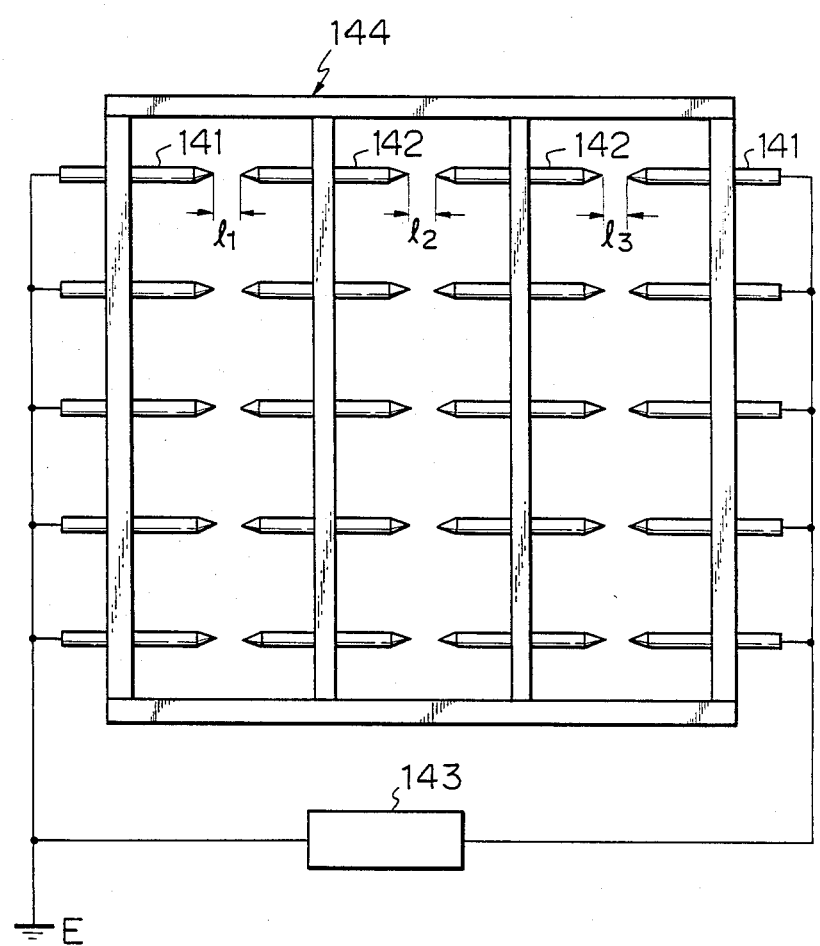
FIG. 14 is a diagrammatic view of a discharge apparatus using intermediate electrodes.

FIG. 14 is a diagrammatic view showing one embodiment of the discharge apparatus used in the present invention. Each of the right and left sides of a support frame 144 is provided with five parallel-connected voltage impressing electrodes 141. The two voltage impressing electrodes 141 lying in the same horizontal plane are so positioned that the tip of one electrode will face the tip of the other. A plurality of intermediate electrodes 142 are disposed on the line connecting the tips of the two opposed electrodes 141. A predetermined gap is provided between each voltage impressing electrode 141 and an adjacent intermediate electrode 142 and between adjacent intermediate electrodes.

The voltage impressing electrodes 141 are preferably in the form of a needle but they may be plates or rods. Needle electrodes are to be positioned such that they face each other at the tip; plate electrodes will face each other at a side edge; and rod electrodes should face each other at the end. The electrodes 141 may be made of any known conductive materials such as iron, aluminum and tungsten.

The intermediate electrodes 142 may also assume a variety of shapes and may be made of a variety of materials. They are preferably in the form of a needle. The intermediate electrodes 142 allow electrical discharges to take place uniformly at individual discharge gaps. The discharge gap length for the embodiment shown in FIG. 14 is the distance between the tip of the voltage impressing electrode 141 on the left side and the tip of the electrode 141 on the right side minus the total length of the intermediate electrodes 142. Therefore, the discharge gap length l is expressed by:

$$l = l_1 + l_2 + l_3$$

(where $l_1$, $l_2$ and $l_3$ are inter-electrode distances as indicated in FIG. 14). In the prior art apparatus, l corresponds to the distance between two voltage impressing electrodes, but in the apparatus of the present invention, l is divided into two or more portions by intermediate electrodes 142. In the embodiment shown in FIG. 14, l is divided into three portions. It may be generally stated that l is divided into (n+1) portions where l is the number of intermediate electrodes lying on the same horizontal line. The values of $l_1$, $l_2$ and $l_3$ may be the same or different and the most stable and uniform discharge will take place if $l_1=l_2=l_3$. The length of each intermediate electrode 142 may be properly selected. The intermediate electrodes 142 are preferably mounted on the support frame 144 in such a manner that they are slidable both rightward and leftward to permit fine tuning of $l_1$, $l_2$ and $l_3$.

The discharge characteristics are influenced by such factors as the discharge gap length, the contour of the electrode surface, and the gap to be treated which is present in the discharge gap. The prior art apparatus is directly exposed to the effects of these factors and has the disadvantage that a discharge occurs selectively at the most sensitive gap if there is a slight difference in the gap length between individual discharge gaps or if there occurs a slight change in the gaseous atmosphere to be treated. In the apparatus of the present invention where the discharge gap length l is divided into two or more portions (four in the case shown in FIG. 14), the effects on the discharge taking place at the gaps $l_1$, $l_2$ and $l_3$ are sufficiently reduced or cancelled to enable uniform discharges to take place in rows of discharge gap length l. This may be better explained by taking as an example the discharge occuring at $l_1$ (assume that the desired discharge has taken place at $l_2$ and $l_3$). Since the proportion of l to the total gap length l is expressed by $l_1/(l_1+l_2+l_3)$, the effects exerted on the discharge by the inter-electrode distances and by the fluid flowing through the gap $l_1$ would be decreased to levels corresponding to $l_1/(l_1+l_2+l_3)$. The same explanation applies to the other gaps $l_2$ and $l_3$. It could therefore be concluded that the greater the number of intermediate electrodes employed, the more uniform the discharge that takes place in each row of electrodes. From a practical view point, however, n cannot be increased too much because l is typically within the range of 1–5 cm and great precision is required in fabricating the apparatus if the values of $l_1$, $l_2$ and $l_3$ become excessively small by dividing the gap length l into too many portions. Therefore, for the purpose of the present invention, n is preferably in the range of 2 to 5.

An a.c. or d.c. voltage may be supplied from a power source 143 to the electrodes 141. The voltage depends on the type of discharge which is intended to be produced in the apparatus of the present invention. Preferably, a voltage no lower than 0.7 kV/mm is applied per unit length of the discharge gap l. The longer the gap l, the higher the voltage that is required. The greater the number of electrodes that are connected in series, the larger the current that is necessary for producing a discharge.

The apparatus of the present invention is capable of producing a corona, spark, glow or arc discharge, with the glow discharge being particularly preferable. The glow discharge is a self-sustaining discharge and is effective in allowing the apparatus of the present invention to exhibit its advantages to the fullest. Needless to say, a uniform arc or spark discharge can be produced in the apparatus of the present invention.

As will be apparent from the foregoing description, one advantage of the discharge apparatus of the present invention wherein each row of discharge gaps is divided into two or more portions by intermediate electrodes is that a uniform discharge field can be formed between parallel-arranged voltage impressing electrodes without connecting resistors as in the prior art apparatus. This uniformity in discharge helps increase the volume efficiency of the apparatus, thereby reducing its overall size. Since no electrical resistor need be used, the greater part of the power input applied contributes to the production of discharges, thereby improving the energy efficiency of the apparatus. If the intermediate electrodes are designed to be slidable, the values of $l_1$, $l_2$ and $l_3$ can be finely adjusted to provide a simple way to establish the conditions for producing uniform discharges.

EXAMPLE 1

This example is intended to demonstrate the effectiveness of the method of the present invention in treating $SO_2$-containing air. A volume of air containing 700 ppm of $SO_2$ and having an absolute humidity of 0.005 kg/kg-dry air was treated at a flow rate of 27 liters/min by the method shown schematically in FIG. 1. The other process conditions were as follows:

Corona discharge:
    Voltage impressed: $-9$ kV (d.c.)
    Discharge current: 200 $\mu$A
Catalytic reaction:
    Catalyst: activated carbon
    SV: $3.6\times 10^4$ hr$^{-1}$
    Temperature: 25° C.

The product air stream contained 466 ppm of $SO_2$, indicating a $SO_2$ removal of 33.3%.

The same procedure was repeated exept that no discharge treatment was effected. The resulting product air stream contained 573 ppm of $SO_2$, indicating a $SO_2$ removal of 18.1%.

EXAMPLES 2 and 3 and COMPARATIVE EXAMPLES 2, 3a and 3b

In these examples, air streams containing toluene and butyl cellosolve were treated. The conditions of the experiments and their results are shown below and in Table 1, respectively.

Glow discharge:
    Flow rate: 10 m$^3$/hr
    Voltage applied: $-10$ kV (d.c.)
    Discharge current: 2 mA
Catalytic reaction:
    Catalyst: Molecular Sieves 13X (trade name of Linde AG)
    SV: $5.5\times 10^4$ hr$^{-1}$
    Temperature: 25° C.

TABLE 1

| Run No. | Noxious component | Treatment | Concentrations of noxious components (ppm) feed | product | Removal (%) | Remarks |
|---|---|---|---|---|---|---|
| Example 2-1 | toluene | discharge and catalytic reaction | 5 | 0 | 100 | 5 ppm ozone added |
| Example 2-2 | toluene | discharge and catalytic reaction | 5 | 1 | 80 | no ozone added |
| Comparative | toluene | discharge | 5 | 2.5 | 50 | no ozone |

TABLE 1-continued

| Run No. | Noxious component | Treatment | Concentrations of noxious components (ppm) feed | product | Removal (%) | Remarks |
|---|---|---|---|---|---|---|
| Example 2 | | alone | | | | added |
| Example 3-1 | butyl cellosolve | discharge and catalytic reaction | 10 | 0 | 100 | 10 ppm ozone added |
| Example 3-2 | butyl cellosolve | discharge and catalytic reaction | 10 | 2 | 80 | no ozone added |
| Comparative Example 3a | butyl cellosolve | discharge alone | 10 | 7 | 70 | 10 ppm ozone added |
| Comparative Example 3b | butyl cellosolve | discharge alone | 10 | 5 | 50 | no ozone added |

EXAMPLE 4 and COMPARATIVE EXAMPLE 4

These examples are intended to compare the method of the present invention and that of the prior art technique with respect to their effectiveness in treating air containing methyl mercaptan. The conditions of the experiments and their results are shown below and in Table 2, respectively.

Discharge:
    Flow rate: 5 m³/hr
    Voltage applied: −10 kV (d.c.)
    Discharge current: 1.8 mA
Catalytic reaction:
    Catalyst: Molecular Sieves 13X (trade name of Linde AG)
    SV: $5.5 \times 10^4$ hr$^{-1}$
    Temperature: 25° C.

TABLE 2

| Run No. | Treatment | Concentrations of methyl mercapton (ppm) feed | product | Removal (%) | Remarks |
|---|---|---|---|---|---|
| Example 4-1 | discharge and catalytic reaction | 120 | ≦1 | 99 | 120 ppm ozone added |
| Example 4-2 | discharge and catalytic reaction | 120 | 2 | 98 | no ozone added |
| Comparative Example 4 | discharge alone | 120 | 20 | 83 | no ozone added |

EXAMPLE 5

Air containing 5 ppm of toluene was treated under the following conditions.

Figure 15:
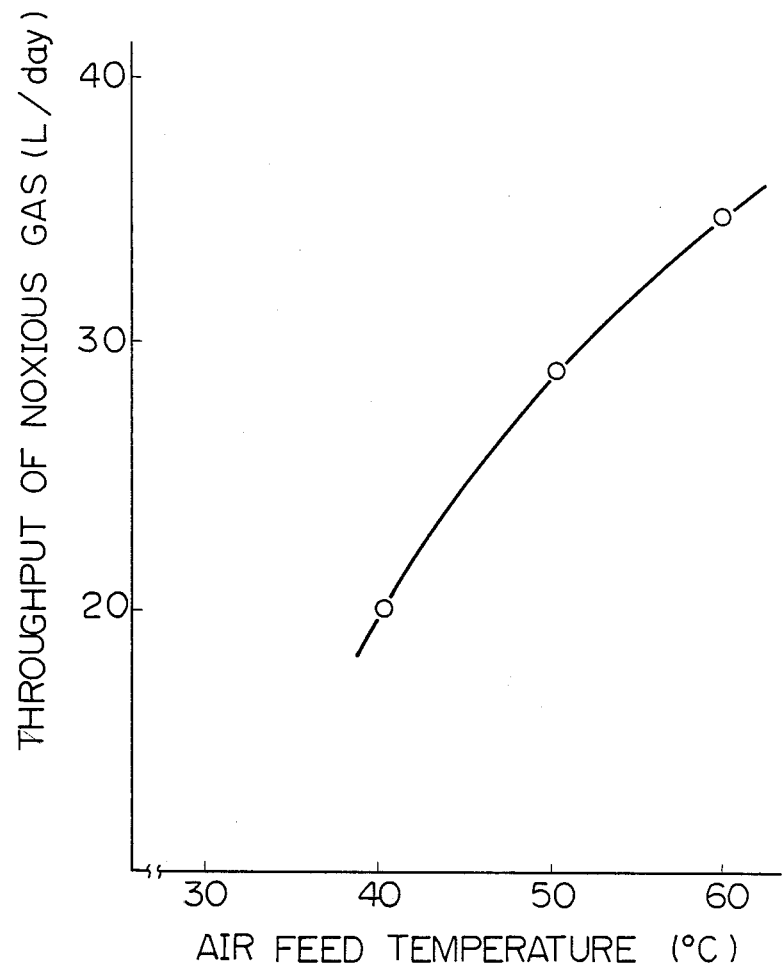
FIG. 15 is a graph showing the results of Example 5.

Glow discharge:
    Temperature of feed air: 20°–60° C.
    Flow rate: 10–30 m³/hr
    Voltage impressed: −10 kV (d.c.)
    Discharge current: 2 mA
Catalytic reaction:
    Catalyst: Molecular Sieves 13X (trade name of Linde AG)
    SV: $40$–$60 \times 10^3$ hr$^{-1}$ The temperature of the air issuing from the catalytic reaction zone was substantially equal to that of the feed into the discharge zone. At selected temperatures, the flow rate was varied and the maximum flow rate that allowed a toluene removal of 99% or higher at each temperature was determined. The results are shown in FIG. 15. The throughputs at 40° C. and 60° C. were about twice and three times as large as the value at ordinary ambient temperature.

EXAMPLES 6 and 7 and COMPARATIVE EXAMPLE 6

A cell suspension containing $2 \times 10^6$ cells/ml of *Saccharomyces formosensis* and *Bacillus subtilis* was sprayed into an air stream flowing at a rate of 12 m³/hr. The air was then treated by the method shown schematically in FIG. 3, with ozone added in an amount of 10 ppm. An apparatus of the type shown in FIG. 14 was employed in the discharge zone. A glow discharge was produced by applying a d.c. voltage of −10 kV between electrodes. Molecular Sieves 3A was used as a catalyst in the catalytic reaction zone. In Comparative Example 6, the same procedure was repeated except that no catalytic reaction was performed. The results are shown below.

TABLE 3

| Run No. | Power input (W) | Concentration of ozone in product (ppm) | Cell concentration in product (number of cells/L) |
|---|---|---|---|
| Example 6 | 40 | 0 | 0 |
| Example 7 | 28 | 0 | 4 |
| Comparative Example 6 | 40 | 0 | 6 |

EXAMPLES 8 and 9 and COMPARATIVE EXAMPLES 8 and 9

Air was subjected to glow discharge with an apparatus of the type shown in FIG. 14. The conditions of the experiments and their results are shown in Table 4.

TABLE 4

| Run No. | Number of series gaps | Number of parallel gaps | Gap length (mm) | Electrode material | Voltage applied (kV) | Average discharge current (mA) | Flow rate at gap (m/sec) | Variation in current (%) |
|---|---|---|---|---|---|---|---|---|
| Example 8 | 3 | 192 | 7 | tungsten | 20 | 80 | 18.5 | 20 |
| Comparative Example 8 | 3 | 192 | 7 | tungsten | 20 | 80 | 1.5 | 40 |
| Example 9 | 2 | 4 | 5 | tungsten | 10 | 10 | 5.3 | 25 |

TABLE 4-continued

| Run No. | Number of series gaps | Number of parallel gaps | Gap length (mm) | Electrode material | Voltage applied (kV) | Average discharge current (mA) | Flow rate at gap (m/sec) | Variation in current (%) |
|---|---|---|---|---|---|---|---|---|
| Comparative Example 9 | 2 | 4 | 5 | tungsten | 10 | 10 | 0.23 | 80 |

Figure 16:
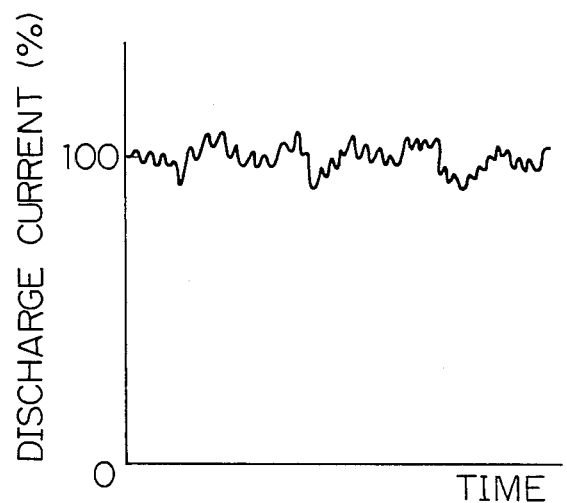
FIGS. 16 and 17 are graphs showing the results of Example 8 and Comparative Example 8a, respectively.
Figure 17:
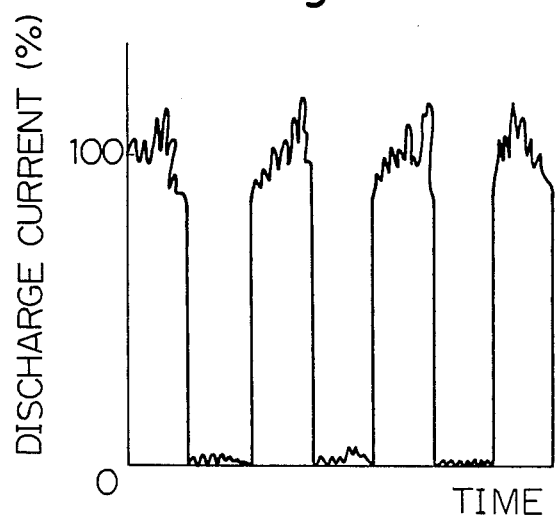

The results of Example 8 are shown in FIG. 16 and those of Comparative Example 8 in FIG. 17. The variation in discharge current was only 20% in Example 8 but was as high as 40% in Comparative Example 8.

EXAMPLE 10

Figure 18:
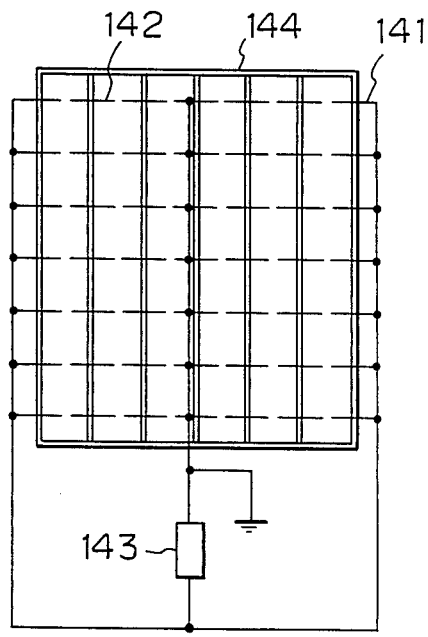
FIG. 18 is a diagrammatic view of the discharge apparatus employed in Example 10.

A discharge apparatus of the type shown in FIG. 18 was tested for its discharge characteristics. The design parameters of the apparatus and the discharging conditions were as follows:

Number of series gaps: 3 per unit
Number of parallel gaps: 7 per unit
Individual gap length: 5 mm
Total gap length: 15 mm
Electrode material: tungsten
Voltage applied: 15 kV a.c.
Total discharge current: 25 mA Air was supplied into the discharge apparatus and it was found that a discharge occurred at each of the discharge gaps.

What is claimed is:

1. A sterilization method which comprises: adding ozone to a gas containing microorganisms; introducing the resulting ozone-containing gas into a discharge zone so as to produce plasma in the gas; and supplying the resulting treated gas into a catalytic reaction zone at ordinary ambient temperature such that a gas which is substantially free from ozone and microorganisms is obtained.

2. A method according to claim 1 wherein said gas is air.

3. A method according to claim 1 wherein the ozone is added in an amount of 10 to 5,000 ppm.

4. A method according to claim 1 wherein a glow or corona discharge is produced in said discharge zone.

5. A method according to claim 1 wherein a catalyst selected from the group consisting of zeolite, a silica-alumina catalyst, activated carbon, and a lead-, zinc-, copper- or nickel-supporting catalyst is employed in said catalytic reaction zone.

6. A sterilization method which comprises: performing surface sterilization in working space by supplying ozone thereinto; after completion of the surface sterilization, drawing the ozone-containing gas from the working space and introducing it into a discharge zone so as to produce plasma in said gas; supplying the resulting treated gas into a catalytic reaction zone at ordinary ambient temperature such that a gas which is substantially free from ozone is obtained; and returning said ozone-free gas to said working space.

7. A method of treating a noxious component in a waste gas by oxidation which comprises first introducing the waste gas into a discharge zone to form a plasma-containing gas and then introducing said plasma-containing gas into a catalytic reaction zone so as to allow said noxious components to enter into a catalytic oxidation reaction.

8. A method according to claim 7 wherein said waste gas is at ordinary ambient temperature.

9. A method according to claim 7 wherein said waste gas has a temperature in the range of 40° to 100° C.

10. A method according to claim 7 wherein a glow or corona discharge is produced in said discharge zone.

11. A method according to claim 7 wherein a catalyst selected from the group consisting of zeolite, a silica-alumina catalyst, activated carbon, and a lead-, zinc-, copper- or nickel-supporting catalyst is employed in said catalytic reaction zone.

12. A method according to claim 7 wherein ozone is added to said waste gas prior to introducing the waste gas into the discharge zone.

13. A method according to claim 7 wherein said noxious component is a malodorous component.

14. A method according to claim 13 wherein said malodorous component is at least one member selected from the group consisting of mercaptan, hydrogen sulfide, ammonia and trimethylamine.

15. A method according to claim 7 wherein said noxious component is an organic solvent.

16. A method according to claim 15 wherein said organic solvent is at least one member selected form the group consisting of enzene, toluene, xylene, ethylene glycol monobutyl ether, methyl ethyl ketone, and methyl isobutyl ketone.

17. A method according to claim 7 wherein said noxious component is a gasous inorganic oxide.

18. A method according to claim 17 wherein said gaseous inorganic oxide is at least one member selected from the group consisting of $NO_x$, $SO_x$ and CO.

* * * * *